United States Patent
Martin

(10) Patent No.: US 8,211,943 B2
(45) Date of Patent: *Jul. 3, 2012

(54) METHOD FOR TREATING A PULMONARY DISEASE STATE IN MAMMALS BY UP REGULATING INDIGENOUS IN VIVO LEVELS OF INFLAMMATORY AGENTS IN MAMMALIAN CELLS

(76) Inventor: Alain Martin, Ringoes, NJ (US)

( * ) Notice: Subject to any disclaimer, the term of this patent is extended or adjusted under 35 U.S.C. 154(b) by 1127 days.

This patent is subject to a terminal disclaimer.

(21) Appl. No.: 12/009,649

(22) Filed: Jan. 22, 2008

(65) Prior Publication Data

US 2009/0041739 A1 Feb. 12, 2009

Related U.S. Application Data

(63) Continuation-in-part of application No. 11/890,911, filed on Aug. 8, 2007, now Pat. No. 8,114,907.

(51) Int. Cl.
*A61K 31/19* (2006.01)

(52) U.S. Cl. .......................................................... 514/557
(58) Field of Classification Search .................... None
See application file for complete search history.

(56) References Cited

U.S. PATENT DOCUMENTS 6,689,810 B2 * 2/2004 Martin .......................... 514/492

* cited by examiner

*Primary Examiner* — Allison Ford
(74) *Attorney, Agent, or Firm* — Craig M. Bell

(57) ABSTRACT

The present invention provides novel methods for treating a pulmonary disease state in mammals by up or down regulating indigenous in vivo levels of an inflammatory agent in mammalian cells comprising contacting the mammalian cells with a therapeutically effective amount of an inflammatory regulator, wherein the inflammatory agent is selected from the group consisting of cytokines, transforming growth factor-$\beta$, elastase, and white blood cells, and wherein the inflammatory regulator is selected from the group consisting of pyruvates and pyruvate precursors.

13 Claims, 10 Drawing Sheets

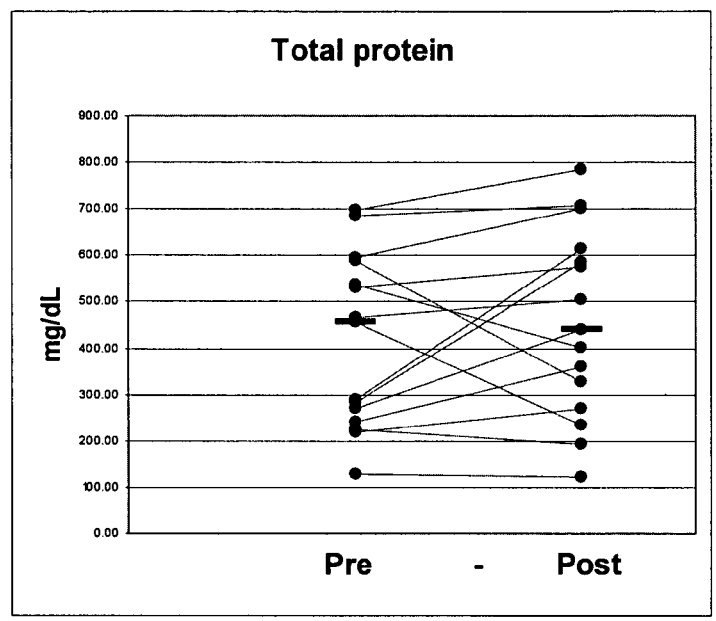
Figure 1. Individual sputum total protein levels before and after study drug inhalation. Slash marks represent the median level.

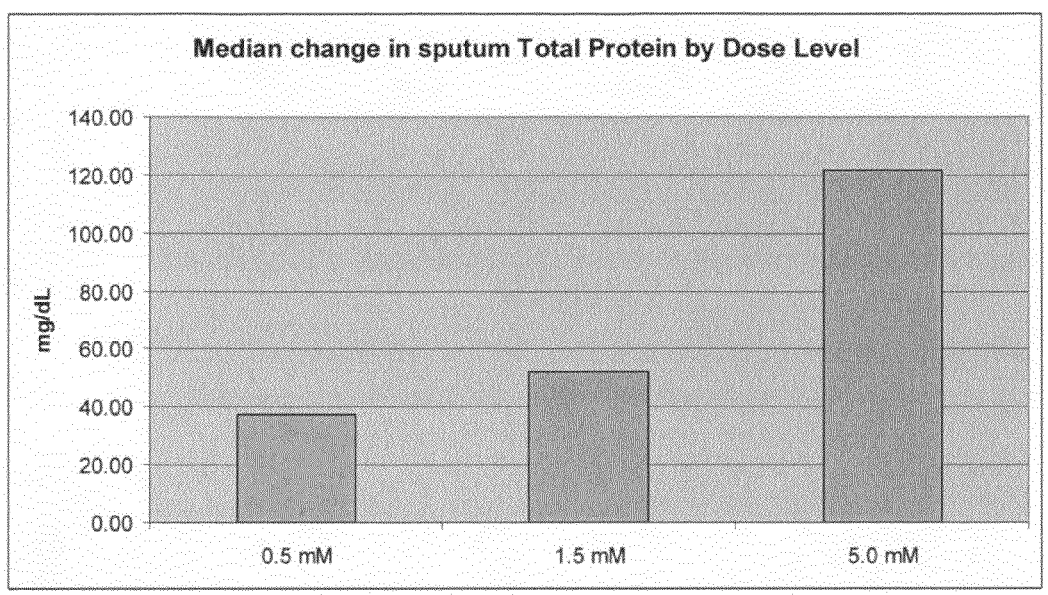
Figure 2. Median change from pre- to post-study drug inhalation in sputum total protein levels and by drug dose level.

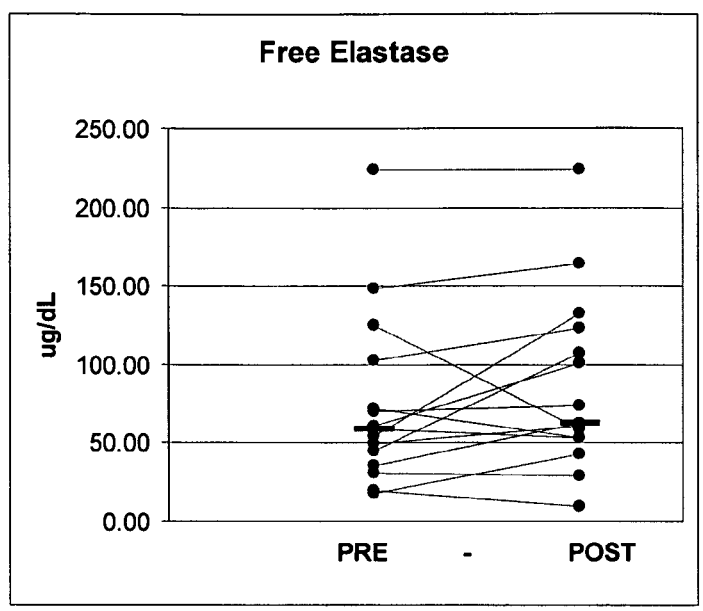
Figure 3. Individual sputum free elastase levels before and after study drug inhalation. Slash marks represent the median level.

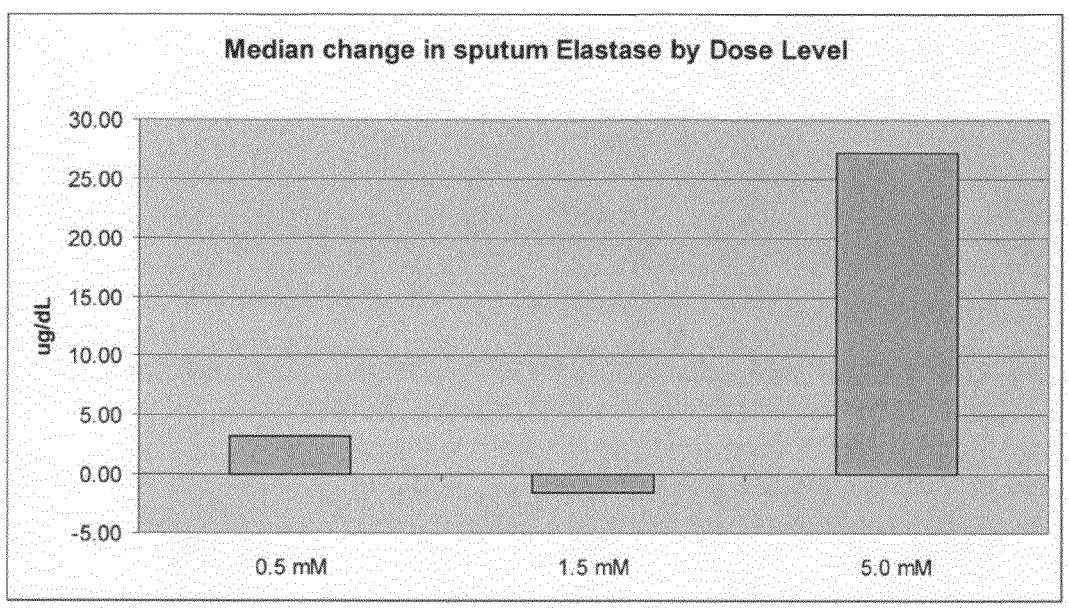
Figure 4. Median change from pre- to post-study drug inhalation in sputum free elastase levels and by drug dose level.

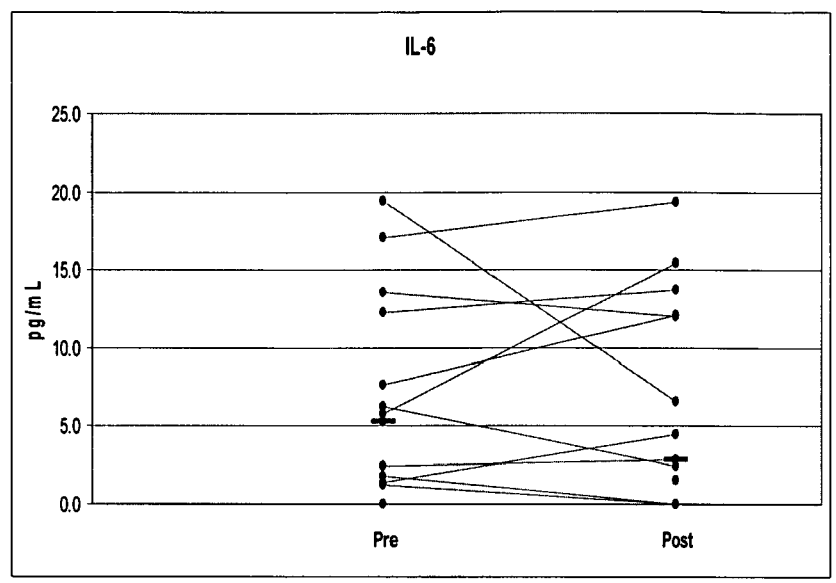
Figure 5. Individual sputum IL-6 levels before and after study drug inhalation. Slash marks represent the median level.

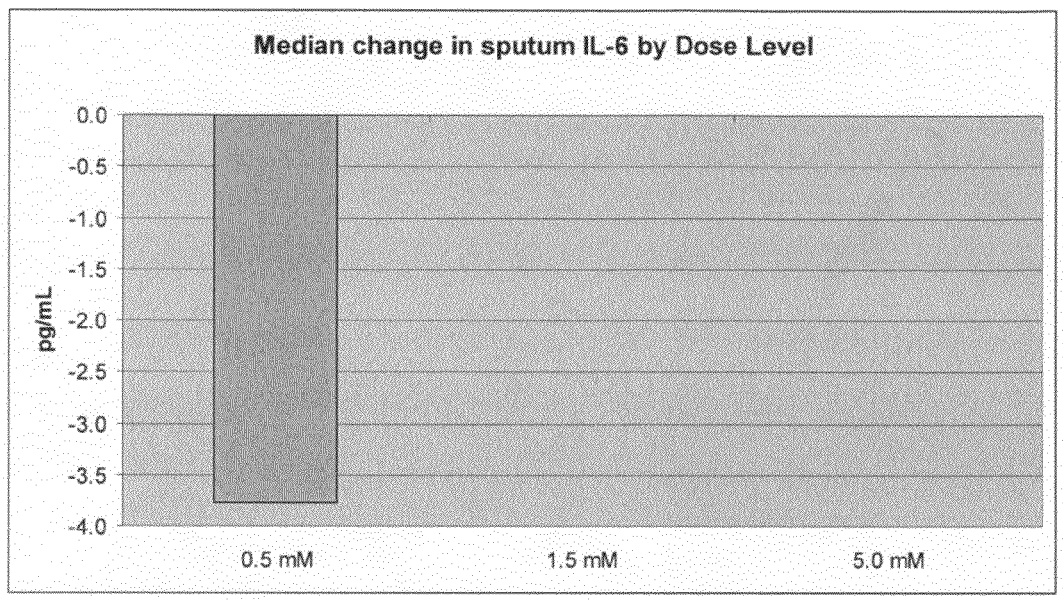
Figure 6. Median change from pre- to post-study drug inhalation in sputum IL-6 levels and by drug dose level.

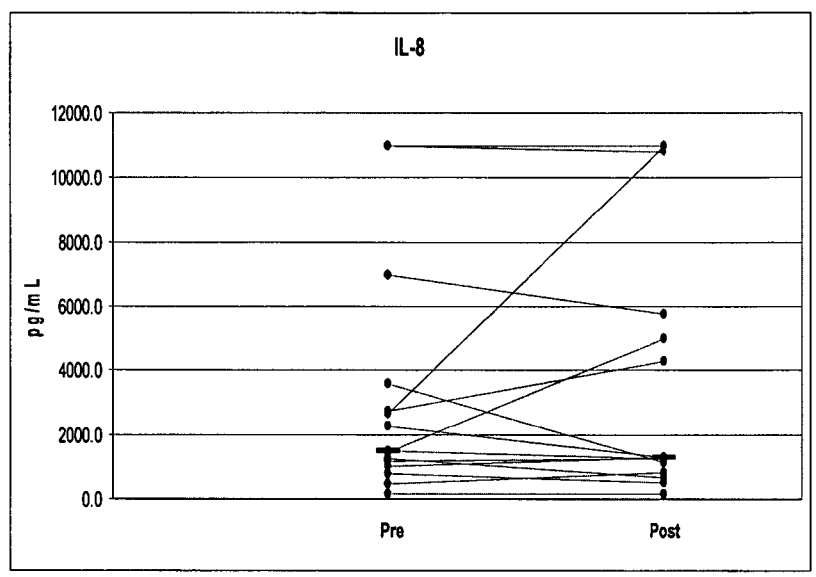
Figure 7. Individual sputum IL-8 levels before and after study drug inhalation. Slash marks represent the median level.

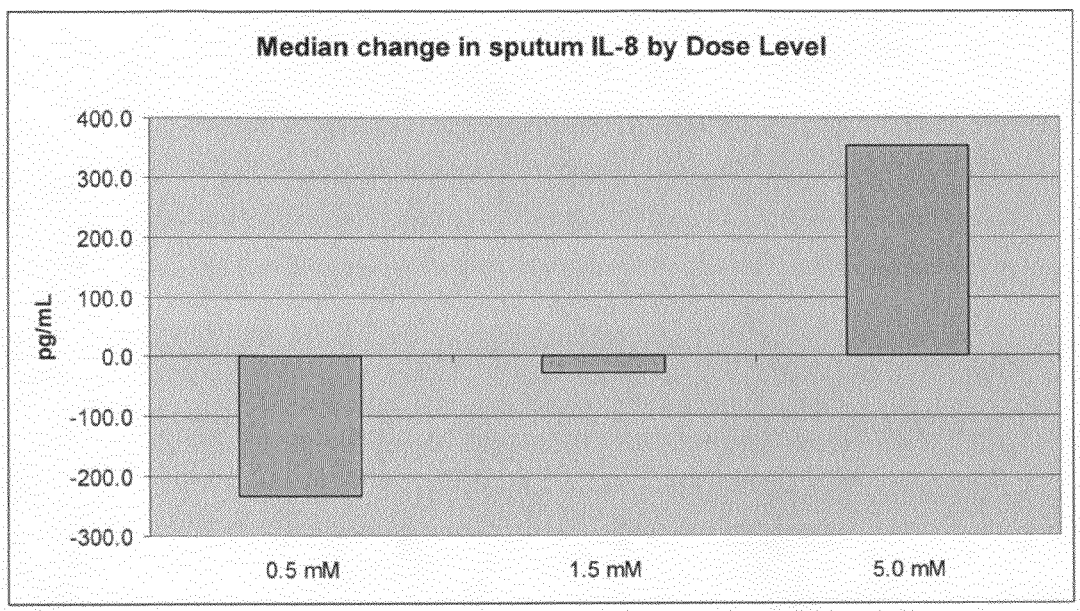
Figure 8. Median change from pre- to post-study drug inhalation in sputum IL-8 levels and by drug dose level.

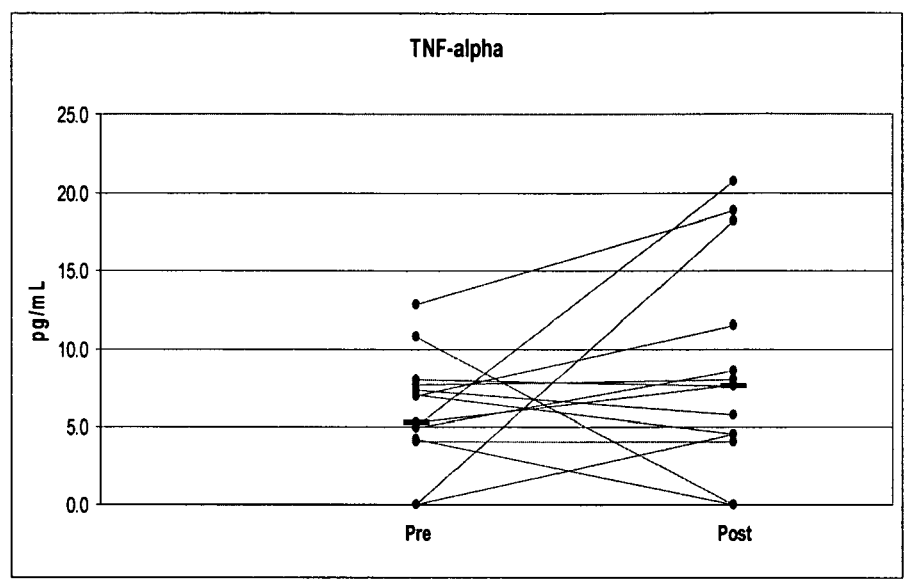
Figure 9. Individual sputum TNF-α levels before and after study drug inhalation. Slash marks represent the median level.

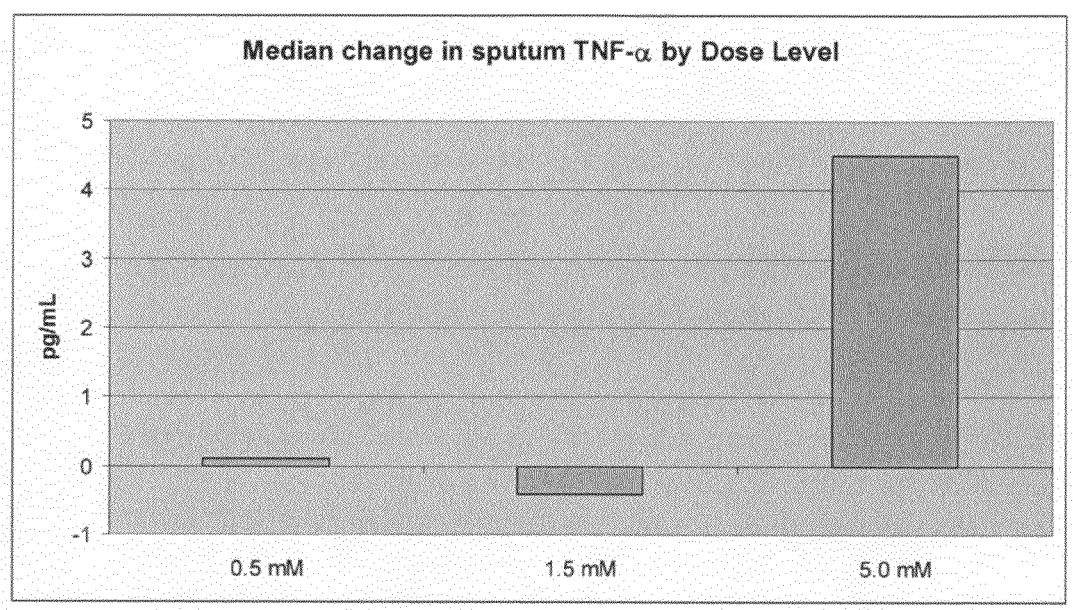
Figure 10. Median change from pre- to post-study drug inhalation in sputum TNF-α levels and by drug dose level.

METHOD FOR TREATING A PULMONARY DISEASE STATE IN MAMMALS BY UP REGULATING INDIGENOUS IN VIVO LEVELS OF INFLAMMATORY AGENTS IN MAMMALIAN CELLS

CROSS-REFERENCE TO RELATED APPLICATIONS

This application is a continuation-in-part of U.S. Ser. No. 11/890,911 filed on Aug. 8, 2007, now U.S. Pat. No. 8,114,907

BACKGROUND OF THE INVENTION

1. Field of the Invention

The present invention provides novel methods for treating a pulmonary disease state in mammals by up or down regulating indigenous in vivo levels of an inflammatory agent in mammalian cells comprising contacting the mammalian cells with a therapeutically effective amount of an inflammatory regulator, wherein the inflammatory agent is selected from the group consisting of cytokines, transforming growth factory, elastase, and white blood cells, and wherein the inflammatory regulator is selected from the group consisting of pyruvates and pyruvate precursors.

2. Background of the Invention

The disclosures referred to herein to illustrate the background of the invention and to provide additional detail with respect to its practice are incorporated herein by reference and, for convenience, are referenced in the following text and respectively grouped in the appended bibliography.

Inflammatory agents are produced by a wide variety of body cells and are natural proteins produced by the cells of the immune system of most vertebrates in response to challenges by foreign agents such as viruses, bacteria, parasites, and tumor cells (1).

Cytokines are a group of proteins and peptides that are used in organisms as signaling compounds and are used to allow one cell to communicate with another. The cytokine family consists mainly of smaller water-soluble proteins and glycoproteins. Cytokines are released by many types of cells, principally activated lymphocytes, and macrophages but also endothelium, epithelium and connective tissue. They are particularly important in both innate and adaptive immune responses. Due to their central role in the immune system, cytokines are involved in a variety of immunological, inflammatory and infectious diseases.

Interleukins (ILs) are a group of inflammatory cytokines that were first seen to be expressed by white blood cells. Interleukins are produced by a wide variety of bodily cells including endothelial cells and macrophages. The family of interleukins includes IL-1 to IL-33. The function of the immune system depends in a large part on interleukins, and rare deficiencies of a number of them have been described, all featuring autoimmune diseases or immune deficiency.

Interferons (IFNs) belong to a large class of glycoproteins and are cytokines. Interferons are natural proteins produced by the cells of the immune system of most vertebrates in response to challenges by foreign agents such as viruses, bacteria, parasites and tumor cells. Interferons assist the immune response by inhibiting viral replication within other cells of the body.

Tumor necrosis factor (TNF) is a cytokine involved in systemic inflammation and is a member of a group of cytokines that all stimulate the acute phase reaction. Tumor necrosis factor causes apoptotic cell death, cellular proliferation, differentiation, inflammation, tumorigenesis, and viral replication. Tumor necrosis factor's primary role is in the regulation of immune cells. Dysregulation and, in particular, overproduction of tumor necrosis factor have been implicated in a variety of human diseases, as well as cancer Chemokines are a family of small cytokines, or proteins that are classified according to shared structural characteristics such as small size (they are all approximately 8-10 kilo Daltons in size), and the presence of four cysteine residues in conserved locations that are key to forming their 3-dimensional shape. Chemokines have the ability to induce directed chemotaxis in nearby responsive cells (chemotactic cytokines). Some chemokines are considered pro-inflammatory and can be induced during an immune response to promote cells of the immune system to a site of infection, while others are considered homeostatic and are involved in controlling the migration of cells during normal processes of tissue maintenance or development. Chemokines exert their biological effects by interacting with G protein-linked transmembrane receptors called chemokine receptors that are selectively found on the surfaces of their target cells.

Cytokines and chemokines have the ability to stimulate leukocyte movement and play an important role in inflammation. Cytokines can influence the synthesis of other cytokines and chemokines. Cytokines can also stimulate cell proliferation acting as growth factors. Cytokines that regulate lymphocyte activation, growth and differentiation include IL-2, IL-4, IL-10, and TNF-$\beta$. Cytokines involved with natural immunity, inflammation, include TNF-$\alpha$, IL-1, INF-$\alpha$, INF-$\beta$, and IL-6. Cytokines that activate inflammatory cells like macrophages include IFN-$\gamma$, TNF-$\alpha$, TNF-$\beta$, IL-5, IL-10, IL-12, and IL-8. Cytokines that stimulate hemopoiesis and mediate immature leukocyte growth and differentiation include IL-3, IL-7, c-kit ligand, granulocyte-macrophage, granulocyte colony-stimulating factor (G-CSF), and stem cell factor. Granulocyte colony-stimulating factor is a glycoprotein, growth factor or cytokine produced by a number of different tissues to stimulate the bone marrow to produce granulocytes and stem cells. Granulocyte colony-stimulating factor then stimulates the bone marrow to pulse them out of the marrow into the blood.

IL-8 is responsible in attracting white blood cells to the site of infection. The major cytokines that mediate inflammation are IL-1, IL-8, and TNF ($\alpha$ and $\beta$). IL-1 and TNF-$\alpha$ are produced by activated macrophages. Their secretion can be stimulated by infections, endotoxins, immune complexes, toxins, physical injury, and a variety of inflammatory processes. Their most important actions in inflammation are their effect on endothelium, leukocytes, and fibroblasts and induction of the systemic acute phase reactions. TNF also cause aggregation and priming of neutrophils, leading to a release of proteolytic enzymes, thus contributing to tissue damage. TNF-$\alpha$, IL-1, and IL-6 also induce the systemic acute phase responses associated with infection, or injury, including fever, loss of appetite, the production of slow wave sleep, release of neutrophils into circulation, release of hormones, hemodynamic effects of septic shock, hypotension, decrease in vascular resistance, increased heart rate, and decrease in blood pH.

An excess of inflammatory agents can increase the production of oxygen radicals, including superoxide anions and hydrogen peroxide, produced during the inflammatory phase of an injury, which will destroy healthy tissue surrounding the site and will mitigate the positive bronchodilation effect of nitric oxide (26). Oxygen radicals can also initiate lipid peroxidation employing arachidonic acid as a substrate producing prostaglandins and leukotrienes. Hydrogen peroxide ($H_2O_2$) can induce arachidonic acid metabolism in alveolar macrophages (17,26). Oxygen radicals also produce 8-isoprostanes, which are potent renal and pulmonary artery vasoconstrictors, bronchoconstrictors, and induce airflow obstructions (26, 27). Because oxygen radicals contribute to the instability of nitric oxide, the addition of superoxide dismutase (SOD) or catalase (15) or Vitamin E (28) protect nitric oxide to produce its desired bronchodilation (2). Hydrogen peroxide is elevated in patients with chronic obstructive pulmonary disease (COPD), asthma, and Acute Respiratory Distress Syndrome (ARDS) (26). A study in 28 patients showed a significant correlation between oxygen radical generation in white blood cell count (WBC) and the degree of bronchial hyperreactivity in vivo in nonallergic patients (18). Thus the ability of pyruvate to regulate inflammation, and inflammatory agents, which can increase the synthesis of oxygen radicals, should reduce the production of oxygen radicals when needed.

Sodium pyruvate is an antioxidant that reacts directly with oxygen radicals to neutralize them. In macrophages, and other cell lines, sodium pyruvate regulates the level of oxygen radicals by acting as an antioxidant and also increases the synthesis of nitric oxide (9). It can specifically lower the overproduction of superoxide anions. Sodium pyruvate also increases cellular levels of glutathione, a major cellular antioxidant (12). It was recently discovered that glutathione is reduced dramatically in antigen-induced asthmatic patients (13) and inhaled glutathione does not readily enter cells. Pyruvate does enter all cells via a transport system and can also cross the blood brain barrier. Excess sodium pyruvate beyond that needed to neutralize oxygen radicals will enter the bronchial and lung cells. All cells have a transport system that allow cells to concentrate pyruvate at higher concentrations than serum levels. In the cell, pyruvate raises the pH level, increases levels of ATP, decreasing levels of ADP and cAMP, and increases levels of GTP, while decreasing levels of cgMP. Nitric oxide (NO) acts in the opposite mode by increasing levels of cGMP and ADP, and requires an acidic pH range in which to work (19). While the above therapeutic compositions and methods are reported to inhibit the production of reactive oxygen intermediates, like hydrogen peroxide or peroxynitrite, none of the disclosures describe methods for treating a pulmonary disease state in mammals by regulating indigenous in vivo levels of inflammatory agents in mammalian cells.

U.S. Pat. No. 6,063,407 (Zapol et al.) discloses methods of treating, inhibiting or preventing vascular thrombosis or arterial restenosis in a mammal. The methods include causing the mammal to inhale a therapeutically effective concentration of gaseous nitric oxide. The inhaled nitric oxide may further comprise compounds that potentiate the beneficial effects of inhaled nitric oxide and antithrombotic agents that complement or supplement the beneficial effects of inhaled nitric oxide.

U.S. Pat. No. 6,020,308 (Dewhirst et al.) discloses the use of an inhibitor of nitric oxide activity, such as a nitric oxide scavenger or a nitric oxide synthase inhibitor, as an adjunct to treatment of inappropriate tissue vascularization disorders.

U.S. Pat. No. 5,891,459 (Cooke et al.) discloses the maintenance or improvement of vascular function and structure by long term administration of physiologically acceptable compounds, such as L-arginine, L-lysine, physiologically acceptable salts thereof, and polypeptide precursors thereof, which enhance the level of endogenous nitric oxide or other intermediates in the nitric oxide induced relaxation pathway in the host. The method further comprises the administration of other compounds, such as B6, folate, B12, or an antioxidant, which provide for short-term enhancement of nitric oxide.

U.S. Pat. No. 5,873,359 (Zapol et al.) discloses a method for treating or preventing bronchoconstriction or reversible pulmonary vasoconstriction in a mammal, which method includes causing the mammal to inhale a therapeutically effective concentration of gaseous nitric oxide or a therapeutically effective amount of a nitric oxide releasing compound and an inhaler device containing nitric oxide gas and/or a nitric oxide releasing compound.

U.S. Pat. No. 5,767,160 (Kaesemeyer) discloses a therapeutic mixture comprising L-arginine and an agonist of nitric oxide synthase, such as nitroglycerin for the treatment of diseases related to vasoconstriction. The vasoconstriction is relieved by stimulating the constitutive form of nitric oxide synthase (cNOS) to produce native nitric oxide. The native nitric oxide has superior beneficial effect when compared to exogenous nitric oxide produced by a L-arginine independent pathway in terms of the ability to reduce clinical endpoints and mortality.

U.S. Pat. No. 5,543,430 (Kaesemeyer) discloses a therapeutic mixture comprising a mixture of L-arginine and an agonist of nitric oxide synthase such as nitroglycerin for the treatment of diseases related to vasoconstriction. The vasoconstriction is relieved by stimulating the constitutive form of nitric oxide synthase to produce native nitric oxide. The native nitric oxide has superior beneficial effect when compared to exogenous nitric oxide produced by a L-arginine independent pathway in terms of the ability to reduce clinical endpoints and mortality.

U.S. Pat. No. 5,428,070 (Cooke et al.) discloses a method for treating atherogenesis and restenosis by long-term administration of physiologically acceptable compounds, which enhance the level of endogenous nitric oxide in the host. Alternatively, or in combination, other compounds may be administered which provide for short-term enhancement of nitric oxide, either directly or by physiological processes. In addition, cells may be genetically engineered to provide a component in the synthetic pathway to nitric oxide, so as drive the process to enhance nitric oxide concentration, particularly in conjunction with the administration of a nitric oxide precursor.

U.S. Pat. No. 5,286,739 (Kilbourn et al.) discloses an anti-hypotensive formulation comprising a mixture of amino acids, which is essentially arginine free or low in arginine (less than about 0.1%, most preferably, about 0.01%). The formulation may include ornithine, citrulline, or both. A method for prophylaxis and treatment of systemic hypotension in an animal is also provided. A method for treating hypotension caused by nitric oxide synthesis through administering a low or essentially arginine free parenteral formulation to an animal, so as to reduce or eliminate nitric oxide synthesis is described. A method for treating an animal in septic shock is also disclosed, comprising administering to the animal an anti-hypotensive formulation comprising a mixture of amino acids, which is essentially arginine free. Prophylaxis or treatment of systemic hypotension, particularly that hypotension incident to chemotherapeutic treatment with biologic response modifiers, such as tumor necrosis factor or interleukin-1 or 2, may be accomplished through the administration of the defined anti-hypotensive formulations until physiologically acceptable systolic blood pressure levels are achieved in the animal. Treatment of an animal for septic shock induced by endotoxin may also be accomplished by administering to the animal the arginine free formulations.

U.S. Pat. No. 5,217,997 (Levere et al.) discloses a method for treating a high vascular resistance disorder in a mammal by administering to a mammalian organism in need of such treatment a sufficient amount of L-arginine or pharmaceutically acceptable salt thereof to treat a high vascular resistance disorder. The L-arginine is typically administered in the range of about 1 mg to 1500 mg per day. High vascular resistance disorders include hypertension, primary or secondary vasospasm, angina pectoris, cerebral ischemia and preeclampsia. Also disclosed is a method for preventing or treating bronchial asthma in a mammal by administering to a mammalian organism in need of such prevention or treatment a sufficient amount of L-arginine to prevent or treat bronchial asthma.

U.S. Pat. No. 5,158,883 (Griffith) discloses pharmaceutically pure physiologically active NG-aminoarginine (i.e., the L or D, L form), or pharmaceutically acceptable salts thereof, administered in a nitric oxide synthesis inhibiting amount to a subject in need of such inhibition (e.g., a subject with low blood pressure or needing immunosuppressive effect) or added to a medium containing isolated organs, intact cells, cell homogenates or tissue homogenates in an amount sufficient to inhibit nitric oxide formation to elucide or control the biosynthesis, metabolism or physiological role of nitric oxide.

U.S. Pat. Nos. 5,798,388, 5,939,459, and 5,952,384 (Katz) pertain to methods for treating various disease states in mammals caused by mammalian cells involved in the inflammatory response and compositions useful in the method. The method comprises contacting the mammalian cells participating in the inflammatory response with an inflammatory mediator. The inflammatory mediator is present in an amount capable of reducing the undesired inflammatory response and is an antioxidant. The preferred inflammatory mediator is a pyruvate. Katz discloses the treatment of airway diseases of the lungs such as bronchial asthma, acute bronchitis, emphysema, chronic obstructive emphysema, centrilobular emphysema, panacinar emphysema, chronic obstructive bronchitis, reactive airway disease, cystic fibrosis, bronchiectasis, acquired bronchiectasis, kartaagener's syndrome; atelectasis, acute atelectasis, chronic atelectasis, pneumonia, essential thrombocytopenia, legionnaires disease, psittacosis, fibrogenic dust disease, diseases due to organic dust, diseases due to irritant gases and chemicals, hypersensitivity diseases of the lung, idiopathic infiltrative diseases of the lungs and the like by inhaling pyruvate containing compositions.

U.S. Pat. No. 5,296,370 (Martin et al.) discloses therapeutic compositions for preventing and reducing injury to mammalian cells and increasing the resuscitation rate of injured mammalian cells. The therapeutic composition comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the resuscitation of injured mammalian cells.

U.S. Pat. No. 6,689,810 (Martin) discloses a therapeutic composition for treating pulmonary diseases states in mammals by altering indigenous in vivo levels of nitric oxide. The therapeutic composition consists of pyruvates, pyruvate precursors, α-keto acids having four or more carbon atoms, precursors of α-keto acids having four or more carbons, and the salts thereof.

U.S. Pat. No. 7,122,578 (Martin) discloses a therapeutic composition for treating topical diseases states and injuries in mammals involving injuries, which cause pain, erythema, swelling, crusting, ischemia, scarring, and excess white blood cell infiltration. The method involves the use of α-keto acids to suppress inflammation.

WO 2006/086643 (Martin) discloses a non-pulmonary treatment of mammalian diseases and injuries caused by the over-expression of peroxynitrite.

While the above therapeutic compositions and methods are reported to inhibit the production of reactive oxygen intermediates, such as hydrogen peroxide, peroxynitrite or nitric oxide, none of the disclosures describe a method for treating a pulmonary disease state in mammals by altering indigenous in vivo levels of inflammatory agents.

SUMMARY OF THE INVENTION

The present invention provides novel methods for treating a pulmonary disease state in mammals by up or down regulating indigenous in vivo levels of an inflammatory agent in mammalian cells comprising contacting the mammalian cells with a therapeutically effective amount of an inflammatory regulator, wherein the inflammatory agent is selected from the group consisting of cytokines, transforming growth factor-β, elastase, and white blood cells, and wherein the inflammatory regulator is selected from the group consisting of pyruvates and pyruvate precursors.

BRIEF DESCRIPTION OF THE DRAWINGS

FIG. 1 is a graph illustrating individual sputum total protein levels before and after study drug inhalation. Slash marks represent the median level.

FIG. 2 is a graph illustrating median change from pre- to post-study drug inhalation in sputum total protein levels and by drug dose level.

FIG. 3 is a graph illustrating individual sputum free elastase levels before and after study drug inhalation. Slash marks represent the median level.

FIG. 4 is a graph illustrating median change from pre- to post-study drug inhalation in sputum free elastase levels and by drug dose level.

FIG. 5 is a graph illustrating individual sputum L-6 levels before and after study drug inhalation. Slash marks represent the median level.

FIG. 6 is a graph illustrating median change from pre- to post-study drug inhalation in sputum IL-6 levels and by drug dose level.

FIG. 7 is a graph illustrating individual sputum IL-8 levels before and after study drug inhalation. Slash marks represent the median level.

FIG. 8 is a graph illustrating median change from pre- to post-study drug inhalation in sputum IL-8 levels and by drug dose level.

FIG. 9 is a graph illustrating individual sputum TNF-α levels before and after study drug inhalation. Slash marks represent the median level.

FIG. 10 is a graph illustrating median change from pre- to post-study drug inhalation in sputum TNF-α levels and by drug dose level.

DETAILED DESCRIPTION OF THE INVENTION

The present invention provides novel methods for treating a pulmonary disease state in mammals by up or down regulating indigenous in vivo levels of an inflammatory agent in mammalian cells comprising contacting the mammalian cells with a therapeutically effective amount of an inflammatory regulator, wherein the inflammatory agent is selected from the group consisting of cytokines, transforming growth factor-β, elastase, and white blood cells, and wherein the inflammatory regulator is selected from the group consisting of pyruvates and pyruvate precursors.

As used herein, the following terms have the given meanings:

The term "injured cell" as used herein refers to a cell which has some or all of the following: (a) injured membranes so that transport through the membranes is diminished and may result in one or more of the following, an increase in toxins and normal cellular wastes inside the cell and/or a decrease in nutrients and other components necessary for cellular repair inside the cell, (b) an increase in concentration of oxygen radicals inside the cell because of the decreased ability of the cell to produce antioxidants and enzymes, and (c) damaged DNA, RNA and ribosomes which must be repaired or replaced before normal cellular functions can be resumed.

The term "pharmaceutically acceptable," such as pharmaceutically acceptable carriers, excipients, etc., refers to pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hydroscopicity, and solubility of compounds. See, e.g., H. Ansel et. al., Pharmaceutical Dosage Forms and Drug Delivery Systems ($6^{th}$ Ed. 1995) at pp. 196 and 1456-1457.

The term "prodrug" or "precursor" refers to compounds, which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bio-reversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The term "therapeutically effective amount" refers to an amount of a therapeutically effective compound, or a pharmaceutically acceptable salt thereof, which is effective to treat, prevent, alleviate or ameliorate symptoms of a disease.

Pyruvates can act as inflammatory mediators (antioxidants) to neutralize oxygen radicals directly, thus lowering the level of inflammation. Pyruvates can also act as antioxidants to regulate the synthesis of nitric oxide. The regulation of oxygen radicals and the synthesis of nitric oxide operate by a different set of genes than those that regulate the synthesis of inflammatory agents such as cytokines and thus operates by a different mechanism. Applicant has discovered that pyruvates and pyruvate precursors can up or down regulate indigenous in vivo levels of inflammatory agents such as cytokines to regulate inflammation. Specifically, applicant has discovered that pyruvates in low dosage amounts, can down regulate the production of inflammatory agents and the number of white blood cells to stop the negative side effects of chronic inflammation in uninfected pulmonary diseases or, in high dosage amounts, can up regulate the production of inflammatory agents and the number of white blood cells needed to kill infections or cancer in infected pulmonary diseases. Mediation of inflammation is very different from the regulation of inflammation. Mediation is a direct chemical effect on the inflammatory components such as the ability of pyruvates to act as antioxidants against oxygen radicals such as hydrogen peroxide, peroxynitrite, or nitric oxide to elicit a response. Regulation of inflammation, such as the up or down regulation of the levels of inflammatory agents, is a direct effect of pyruvates to elicit a response on a genetic level and to specifically effect and regulate the function of inflammatory cells such as white blood cells. The ability to regulate cellular functions of inflammatory cells is very different from the ability to directly chemically affect an oxygen radical. Both will lower inflammation, but only inflammatory regulators can up or down regulate the level of inflammation.

Pyruvates and pyruvate precursors control the positive and negative effects of inflammatory agents such as cytokines, transforming growth factor-$\beta$, elastase, and white blood cells at higher levels. Too high a number of white blood cells and other inflammatory agents is detrimental to lungs. Pyruvates and pyruvate precursors will lower and protect cells and organs from excess inflammatory agents and white blood cell numbers when they are high and infections are not involved. Moderate to severe asthmatics and emphysema patients produce much higher levels of inflammatory agents including oxygen radicals especially in smokers and low dosages of pyruvates produce better results in these patients by lowering excess levels of inflammatory agents. The ability to control the levels of inflammation is important. Over production or under production is detrimental and produces various diseases in both the lungs and nasal cavities. Dosages of 5 ml of 0.5 mM pyruvates reduce the inflammatory markers in patients with lung diseases and can be used in diseases where inflammation is a problem, i.e., in smokers (21), mild asthmatics (21), in intubated or tracheostomized patients (19), in normal subjects after exercise and hyperventilation (21), COPD patients (22), and in patients with cystic fibrosis (22) with kartagener's syndrome (22), moderate or severe asthma (22), sarcoidosis (22), and fibrosing alveolitis (22). Increased levels of inflammatory cytokines especially IL-8, which is a neutrophil activating cytokine, are chemotactic for eosinophils, which produce and enhance inflammation (20). Acute treatment with corticosteroids during an exacerbation of asthma is associated with a decline in inflammatory markers in adults and children (23).

In contrast, higher dosages of pyruvates can increase the number of white blood cells and the synthesis of cytokines needed in diseases where cytokines are abnormally low, such as in infections. Dosages of 5 ml of 5 mM pyruvates or higher beyond that needed to neutralize oxygen radicals will enter the bronchial and lung cells and increase the levels of white blood cells and IL-1, IL-6, IL-8, TNF-α, elastase to help fight infections. All cells have a transport system that allow cells to concentrate pyruvate at higher concentrations than serum levels. In the cell, pyruvate raises the pH level, increases levels of ATP, decreasing levels of ADP and cAMP, and increases levels of GTP, while decreasing levels of cGMP.

In summary, pyruvate enhances the body's ability to reduce inflammation or to increase it to fight infections and tumors. The combination of pyruvate alone or in combination with other drugs are effective for the treatment of lung diseases such as asthma, emphysema etc, where inflammation is high, and in the treatment of tumors, bacterial infections, fungal infections, viral infections, angina, ischemic diseases, and congestive heart failure, where inflammation is low.

The pulmonary diseases suitable for treatment by the cytokine regulators of the present invention include, but are not limited to, bronchial asthma, acute bronchitis, emphysema, chronic obstructive emphysema, chronic obstructive pulmonary disease, centrilobular emphysema, panacinar emphysema, chronic obstructive bronchitis, smoker's disease, reactive airway disease, cystic fibrosis, bronchiectasis, acquired bronchiectasis, kartaagener's syndrome, acelectasis, acute atelectasis, chronic acelectasis, pneumonia, essential thrombocytemia, legionnaire's disease, psittacosis, fibrogenic dust disease, hypersensitivity diseases of the lung, idiopathic infiltrative diseases of the lungs, chronic obstructive pulmonary disorder, adult respiratory distress syndrome, pulmonary tumors, and diseases caused by organic dust, irritant gases, and chemicals. Preferred disease states are cystic fibrosis, bronchial asthma, and chronic obstructive pulmonary disease.

The pulmonary tumors suitable for treatment by the cytokine regulators of the present invention include, but are not limited to, epidermoid (squamous cell) carcinoma, small cell (oat cell) carcinoma, adenocarcinoma, and large cell (anaplastic) carcinoma.

The inflammatory agent in the present invention may be selected from a wide variety of inflammatory agents. Preferred inflammatory agents are cytokines, transforming growth factor-β, elastase, and white blood cells. Preferred cytokines may be selected from the group consisting of interleukin-1, interleukin-2, interleukin-4, interleukin-6, interleukin-8, interleukin-10, interleukin-17, and interleukin-23. More preferred cytokines are interleukin-1, interleukin-6, and interleukin-8. IL-10, IL-17, and IL-23 are all regulated by the levels of IL-6 and IL-8 and so regulation of IL-6 and IL-8 can regulate IL-10, IL-17, and IL-23.

Another preferred cytokine is tumor necrosis factor-α. Tumor necrosis factor-α is a cytokine involved in systemic inflammation and is a member of a group of cytokines that all stimulate the acute phase reaction.

Another preferred cytokine is interferon-α and interferon-β. Interferons are glycoproteins that assist the immune response by inhibiting viral replication within other cells of the body.

Another preferred inflammatory agent is transforming growth factor-β (TGF-β). Transforming growth factor-β regulates growth and proliferation of cells, blocking the growth of many different cell types including tumor cells.

Another preferred inflammatory agent is elastase. Elastase is an enzyme that digests and degrades a number of proteins including elastin, an elastic substance found in the lungs and other organs.

Another preferred inflammatory agent is white blood cells. White blood cells or leukocytes are cells of the immune system, which defend the body against both infectious disease and foreign materials. Several different and diverse types of leukocytes exist, however they are all produced and derived from a pluripotent cell in the bone marrow known as a hematopoietic stem cell. Leukocytes are found throughout the body, including the blood and lymphatic system.

The inflammatory regulators in the present invention are pyruvates and pyruvate precursors. Non-limiting illustrative examples of pyruvates include pyruvic acid, lithium pyruvate, sodium pyruvate, potassium pyruvate, magnesium pyruvate, calcium pyruvate, zinc pyruvate, manganese pyruvate, aluminum pyruvate, ammonium pyruvate, and mixtures thereof. Non-limiting illustrative examples of pyruvate precursors include pyruvyl-glycine, pyruvyl-alanine, pyruvyl-leucine, pyruvyl-valine, pyruvyl-isoleucine, pyruvyl-phenylalanine, pyruvamide, salts of pyruvic acid, and mixtures thereof.

The amount of the inflammatory regulator present in the therapeutic compositions of the present invention is a therapeutically effective amount. A therapeutically effective amount of the inflammatory regulator is that amount of the inflammatory agent necessary to treat the pulmonary disease. The exact amount of inflammatory regulator is a matter of preference subject to such factors as the type of inflammatory regulator being employed, the type of condition being treated as well as the other ingredients in the composition. The exact amount of inflammatory regulator will also be determined by whether the pulmonary disease is infected or uninfected. In general, the dosage of the inflammatory regulator may range from about 0.0001 mg to about 1 gram, preferably from about 0.001 mg to about 0.8 gram, and more preferably from about 0.01 mg to about 0.6 gram.

In another embodiment, the pyruvate or pyruvate precursor inflammatory regulator further may further comprise α-keto-isovaleric acid, or a precursor thereof. In general, the dosage of α-keto-isovaleric acid may range from about 0.0001 mg to about 1 gram, preferably from about 0.001 mg to about 0.8 gram, and more preferably from about 0.01 mg to about 0.6 gram.

In one embodiment, the level of inflammatory agents in the mammalian cells is abnormally low in the disease state. In another embodiment, the level of inflammatory agents in the mammalian cells is abnormally high in the disease state.

Whether the levels of inflammatory agents that are abnormally low or abnormally high can be determined from the level of inflammatory agents in a patient's lungs and sputum.

In many cases, pulmonary diseases produce infections that these inflammatory regulators can treat. Such infections may be bacterial, viral, or fungal. The inflammatory regulators may be inhaled first to regulate inflammatory agents followed by inhalation of a therapeutic agent. The therapeutic agent may be administered prior to, concomitantly with, or after administration of the inflammatory regulator. The therapeutic agent may be selected from the group consisting of antibacterials, antivirals, antifungals, antitumors, antihistamines, proteins, enzymes, hormones, nonsteroidal anti-inflammatories, cytokines, nicotine, insulin, and steroids.

The antibacterial agents which may be employed in the therapeutic compositions may be selected from a wide variety of water-soluble and water-insoluble drugs, and their acid addition or metallic salts, useful for treating pulmonary diseases. Both organic and inorganic salts may be used provided the antibacterial agent maintains its medicament value. The antibacterial agents may be selected from a wide range of therapeutic agents and mixtures of therapeutic agents, which may be administered in sustained release or prolonged action form. Nonlimiting illustrative specific examples of antibacterial agents include bismuth containing compounds, sulfonamides; nitrofurans, metronidazole, tinidazole, nimorazole, benzoic acid; aminoglycosides, macrolides, penicillins, polypeptides, tetracyclines, cephalosporins, chloramphenicol, and clidamycin. Preferably, the antibacterial agent is selected from the group consisting of bismuth containing compounds, such as, without limitation, bismuth aluminate, bismuth subcitrate, bismuth subgalate, bismuth subsalicylate, and mixtures thereof; the sulfonamides; the nitrofurans, such as nitrofurazone, nitrofurantoin, and furozolidone; and miscellaneous antibacterials such as metronidazole, tinidazole, nimorazole, and benzoic acid; and antibiotics, including the aminoglycosides, such as gentamycin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bacitracin and polymyxin; the tetracyclines, such as tetracycline, chlorotetracycline, oxytetracycline, and doxycycline; the cephalosporins, such as cephalexin and cephalothin; and miscellaneous antibiotics, such as chloramphenicol, and clidamycin. More preferably, the antibacterial agent is selected from the group consisting of bismuth aluminate, bismuth subcitrate, bismuth subgalate, bismuth subsalicylate, sulfonamides, nitrofurazone, nitrofurantoin, furozolidone, metronidazole, tinidazole, nimorazole, benzoic acid, gentamycin, neomycin, kanamycin, streptomycin, erythromycin, clindamycin, rifamycin, penicillin G, penicillin V, Ampicillin amoxicillin, bacitracin, polymyxin, tetracycline, chlorotetracycline, oxytetracycline, doxycycline, cephalexin, cephalothin, chloramphenicol, and clidamycin.

The amount of antibacterial agent which may be employed in the therapeutic compositions of the present invention may vary depending upon the therapeutic dosage recommended or permitted for the particular antibacterial agent. In general, the amount of antibacterial agent present is the ordinary dosage required to obtain the desired result. Such dosages are known to the skilled practitioner in the medical arts and are not a part of the present invention. In a preferred embodiment, the antibacterial agent in the therapeutic composition is present in an amount from about 0.01% to about 10%, preferably from about 0.1% to about 5%, and more preferably from about 1% to about 3%, by weight.

The antiviral agents which may be employed in the therapeutic compositions may be selected from a wide variety of water-soluble and water-insoluble drugs, and their acid addition or metallic salts, useful for treating pulmonary diseases. Both organic and inorganic salts may be used provided the antiviral agent maintains its medicament value. The antiviral agents may be selected from a wide range of therapeutic agents and mixtures of therapeutic agents, which may be administered in sustained release or prolonged action form. Nonlimiting illustrative categories of such antiviral agents include RNA synthesis inhibitors, protein synthesis inhibitors, immunostimulating agents, protease inhibitors, and cytokines. Nonlimiting illustrative specific examples of such antiviral agents include the following medicaments.

(a) Acyclovir (9-[(2-hydroxyethyloxy)methyl]guanine, ZOVIRAX®) is a white, crystalline powder with a molecular weight of 225 Daltons and a maximum solubility in water of 2.5 mg/mL at 37° C. Acyclovir is a synthetic purine nucleoside analogue with in vitro and in vivo inhibitory activity against human herpes viruses including herpes simplex types 1 (HSV-1) and 2 (HSV-2), varicella-zoster virus (VZV), Epstein-Barr virus (EBV), and cytomegalovirus (CMV).

(b) Foscarnet sodium (phosphonoformic acid trisodium salt, FOSCAVIR®) is a white, crystalline powder containing 6 equivalents of water of hydration with an empirical formula of $Na_3CO_6P_6H_2O$ and a molecular weight of 300.1. Foscarnet sodium has the potential to chelate divalent metal ions such as calcium and magnesium, to form stable coordination compounds. Foscarnet sodium is an organic analogue of inorganic pyrophosphate that inhibits replication of all known herpes viruses in vitro including cytomegalovirus (CMV), herpes simplex virus types 1 and 2 (HSV-1, HSV-2), human herpes virus 6 (HHV-6), Epstein-Barr virus (EBV), and varicella-zoster virus (VZV), Foscarnet sodium exerts its antiviral activity by a selective inhibition at the pyrophosphonate binding site on virus-specific DNA polymerases and reverse transcriptases at concentrations that do not affect cellular DNA polymerases.

(c) Ribavirin (1-β-D-ribofuranosyl-1,2,4-triazole-3-carboxamide, VIRAZOLE®) is a synthetic nucleoside which is a stable, white, crystalline compound with a maximum solubility in water of 142 mg/ml at 25° C. and with only a slight solubility in ethanol. The empirical formula is $C_8H_{12}N_4O_5$ and the molecular weight is 244.2 Daltons. Ribavirin has antiviral inhibitory activity in vitro against respiratory syncytial virus, influenza virus, and herpes simplex virus. Ribavirin is also active against respiratory syncytial virus (RSV) in experimentally infected cotton rats. In cell cultures, the inhibitory activity of ribavirin for RSV is selective. The mechanism of action is unknown. Reversal of the in vitro antiviral activity by guanosine or xanthosine suggests ribavirin may act as an analogue of these cellular metabolites.

(d) Vidarabine (adenine arabinoside, Ara-A, 9-β-D-arabinofuranosyladenine monohydrate, VIRA-A®) is a purine nucleoside obtained from fermentation cultures of *Streptomyces antibioticus*. Vidarabine is a white, crystalline solid with the empirical formula, $C_{10}H_{13}N_5O_4H_2O$. The molecular weight of vidarabine is 285.2, the solubility is 0.45 mg/ml at 25° C., and the melting point ranges from 260° C. to 270° C. Vidarabine possesses in vitro and in vivo antiviral activity against Herpes simplex virus types 1 and 2 (HSV-1 and HSV-2), and in vitro activity against varicella-zoster virus (VZV). The antiviral mechanism of action has not yet been established. Vidarabine is converted into nucleotides, which inhibit viral DNA polymerase.

(e) Ganciclovir sodium (9-(1,3-dihydroxy-2-propoxymethyl) guanine, monosodium salt, CYTOVENE®, CYMEVENE®) is an antiviral drug active against cytomegalovirus for intravenous administration. Ganciclovir sodium has a molecular formula of $C_9H_{12}N_6NaO_4$ and a molecular weight of 277.21. Ganciclovir sodium is a white lyophilized powder with an aqueous solubility of greater than 50 mg/mL at 25° C. Ganciclovir is a synthetic nucleoside analogue of 2'-deoxyguanosine that inhibits replication of herpes viruses both in vitro and in vivo. Sensitive human viruses include cytomegalovirus (CMV), herpes simplex virus-1 and -2 (HSV-1, HSV-2), Epstein-Barr virus (EBV), and varicella zoster virus (VZV).

(f) Zidovudine [azidothymidine (AZT), 3'-azido-3'-deoxythymidine, RETROVIR®] is an antiretroviral drug active against human immunodeficiency virus (HIV) for oral administration. Zidovudine is a white to beige, odorless, crystalline solid with a molecular weight of 267.24 Daltons and a molecular formula of $C_{10}H_{13}N_5O_4$. Zidovudine is an inhibitor of the in vitro replication of some retroviruses including HIV (also known as HTLV III, LAV, or ARV). Zidovudine is a thymidine analogue in which the 3'-hydroxy (—OH) group is replaced by an azido (—$N_3$) group.

(g) Phenol (carbolic acid) is a topical antiviral, anesthetic, antiseptic, and antipruritic drug. Phenol is a colorless or white crystalline mass, which is soluble in water, has a characteristic odor, a molecular formula of $C_6H_6O$, and a molecular weight of 94.11.

(h) Amantadine hydrochloride (1-adamantanamine hydrochloride, SYMMETREL®) has pharmacological actions as both an anti-Parkinson and an antiviral drug. Amantadine hydrochloride is a stable white or nearly, white crystalline powder, freely soluble in water and soluble in alcohol and in chloroform. The antiviral activity of amantadine hydrochloride against influenza A is not completely understood but the mode of action appears to be the prevention of the release of infectious viral nucleic acid into the host cell.

(i) Interferon α-n3 (human leukocyte derived, ALFERON®) is a sterile aqueous formulation of purified, natural, human interferon α proteins for use by injection. Interferon α-n3 injection consists of interferon a proteins comprising approximately 166 amino acids ranging in molecular weights from 16,000 to 27,000 Daltons. Interferons are naturally occurring proteins with both antiviral and antiproliferative properties.

(j) Interferon α-2a (recombinant, ROFERON-A®) is a sterile protein product for use by injection. Interferon α-2a is a highly purified protein containing 165 amino acids, and it has an approximate molecular weight of 19,000 Daltons. The mechanism by which Interferon α-2a, recombinant, exerts antitumor or antiviral activity is not clearly understood. However, it is believed that direct antiproliferative action against tumor cells, inhibition of virus replication, and modulation of the host immune response play important roles in antitumor and antiviral activity.

(k) Oseltamivir ((3R,4R,5 S)-4-acetylamino-5-amino-3-(1-ethylpropoxy)-1-cyclohexene-1-carboxylic acid ethyl ester, TAMIFLU®) is a is an antiviral drug that is used in the treatment and prophylaxis of both influenza virus A and Influenza virus B. Oseltamivir is a neuraminidase inhibitor. It acts as a transition-state analogue inhibitor of influenza neuraminidase, preventing new viruses from emerging from infected cells. Oseltamivir has a molecular formula of $C_{16}H_{28}N_2O_4$.

Preferred antiviral agents to be employed may be selected from the group consisting of acyclovir, foscarnet sodium, ribavirin, vidarabine, ganciclovir sodium, zidovudine, phenol, amantadine hydrochloride, and interferon α-n3, interferon α-2a, and oseltamivir. In a preferred embodiment, the antiviral agent is selected from the group consisting of acyclovir, foscarnet sodium, ribavirin, vidarabine, and ganciclovir sodium. In a more preferred embodiment, the antiviral agent is acyclovir.

The amount of antiviral agent which may be employed in the therapeutic compositions of the present invention may vary depending upon the therapeutic dosage recommended or permitted for the particular antiviral agent. In general, the amount of antiviral agent present is the ordinary dosage required to obtain the desired result. Such dosages are known to the skilled practitioner in the medical arts and are not a part of the present invention. In a preferred embodiment, the antiviral agent in the therapeutic composition is present in an amount from about 0.1% to about 20%, preferably from about 1% to about 10%, and more preferably from about 2% to about 7%, by weight.

The antifungal agents which may be employed in the therapeutic compositions may be selected from a wide variety of water-soluble and water-insoluble drugs, and their acid addition or metallic salts, useful for treating pulmonary diseases. Both organic and inorganic salts may be used provided the antifungal agent maintains its medicament value. The antifungal agents may be selected from a wide range of therapeutic agents and mixtures of therapeutic agents, which may be administered in sustained release or prolonged action form. Nonlimiting illustrative specific examples of antifungal agents include the following medicaments: miconazole, clotrimazole, tioconazole, terconazole, povidone-iodine, and butoconazole. Other antifungal agents are lactic acid and sorbic acid. Preferred antifungal agents are miconazole and clotrimazole.

The amount of antifungal agent, which may be employed in the therapeutic compositions of the present invention may vary depending upon the therapeutic dosage recommended or permitted for the particular antifungal agent. In general, the amount of antifungal agent present is the ordinary dosage required to obtain the desired result. Such dosages are known to the skilled practitioner in the medical arts and are not a part of the present invention. In a preferred embodiment, the antifungal agent in the therapeutic composition is present in an amount from about 0.05% to about 10%, preferably from about 0.1% to about 5%, and more preferably from about 0.2% to about 4%, by weight.

The antitumor agents which may be employed in the therapeutic compositions may be selected from a wide variety of water-soluble and water-insoluble drugs, and their acid addition or metallic salts, useful for treating pulmonary diseases. Both organic and inorganic salts may be used provided the antitumor agent maintains its medicament value. The antitumor agents may be selected from a wide range of therapeutic agents and mixtures of therapeutic agents, which may be administered in sustained release or prolonged action form. Nonlimiting illustrative specific examples include anti-metabolites, antibiotics, plant products, hormones, and other miscellaneous chemotherapeutic agents. Chemically reactive drugs having nonspecific action include alkylating agents and N-alkyl-N-nitroso compounds. Examples of alkylating agents include nitrogen mustards, azridines (ethylenimines), sulfonic acid esters, and epoxides. Anti-metabolites are compounds that interfere with the formation or utilization of a normal cellular metabolite and include amino acid antagonists, vitamin and coenzyme antagonists, and antagonists of metabolites involved in nucleic acid synthesis such as glutamine antagonists, folic acid antagonists, pyrimidine antagonists, and purine antagonists. Antibiotics are compounds produced by microorganisms that have the ability to inhibit the growth of other organisms and include actinomycins and related antibiotics, glutarimide antibiotics, sarkomycin, fumagillin, streptonigrin, tenuazonic acid, actinogan, peptinogan, and anthracyclic antibiotics such as doxorubicin. Plant products include colchicine, podophyllotoxin, and vinca alkaloids. Hormones include those steroids used in breast and prostate cancer and corticosteriods used in leukemias and lymphomas. Other miscellaneous chemotherapeutic agents include urethane, hydroxyurea, and related compounds; thiosemicarbazones and related compounds; phthalanilide and related compounds; and triazenes and hydrazines. The anticancer agent may also be a monoclonal antibody or the use of X-rays. In a preferred embodiment, the anticancer agent is an antibiotic. In a more preferred embodiment, the anticancer agent is doxorubicin. In a most preferred embodiment, the anticancer agent is doxorubicin.

The amount of antitumor agent, which may be employed in the therapeutic compositions of the present invention may vary depending upon the therapeutic dosage recommended or permitted for the particular antitumor agent. In general, the amount of antitumor agent present is the ordinary dosage required to obtain the desired result. Such dosages are known to the skilled practitioner in the medical arts and are not a part of the present invention. In a preferred embodiment, the antitumor agent in the therapeutic composition is present in an amount from about 1% to about 50%, preferably from about 10% to about 30%, and more preferably from about 20% to about 25%, by weight.

Nicotine is an alkaloid found predominantly in tobacco and constitutes about 0.6-3% of tobacco by dry weight. In low concentrations, an average cigarette yields about 1 mg of absorbed nicotine. Nicotine acts as a stimulant in mammals and is one of the main factors responsible for the dependence-forming properties of tobacco smoking. Nicotine is a hygroscopic, oily liquid that is miscible with water in its base form. As a nitrogenous base, nicotine forms salts with acids that are usually solid and water-soluble. The primary therapeutic use of nicotine is in treating nicotine dependence in order to eliminate smoking with its health risks.

Insulin is an animal hormone, produced in the pancreas, whose presence informs the body's cells that the animal is well fed, causing liver and muscle cells to take in glucose and store it in the form of glycogen, and causing fat cells to take in blood lipids and turn them into triglycerides. Insulin is used medically to treat some forms of diabetes mellitus. Patients with type 1 diabetes mellitus depend on external insulin (most commonly injected subcutaneously) for their survival because of the absence of the hormone. Patients with type 2 diabetes mellitus have insulin resistance, relatively low insulin production, or both; some type 2 diabetics eventually require insulin when other medications become insufficient in controlling blood glucose levels. Insulin is a peptide hormone composed of 51 amino acid residues. Insulin's genetic structure varies marginally between species of animal. Bovine insulin differs from human in only three amino acid residues, and porcine insulin in one. Even insulin from some species of fish is similar enough to human to be effective in humans. The C-peptide of proinsulin, however, is very divergent from species to species. All structures of insulin useful in humans, including synthetic "human" insulin, may be employed in the present invention. Unlike many medicines, insulin cannot be taken orally. Like nearly all proteins introduced into the gastrointestinal tract, insulin is degraded losing all insulin activity. Insulin is usually taken as subcutaneous injections or may be inhaled.

The carrier composition is selected from the group consisting of tablets, capsules, liquids, isotonic liquids, isotonic media, enteric tablets and capsules, parenterals, topicals, creams, gels, ointments, chewing gums, confections and the like. The favored method of delivery is through inhalation by mouth or sinuses.

Obviously, numerous modifications and variations of the present invention are possible in the light of the above teachings and the invention is not limited to the examples herein. It is therefore understood that within the scope of the appended claims, the invention may be practiced otherwise than as specifically described herein.

Throughout this application, various publications have been referenced. The disclosures in these publications are incorporated herein by reference in order to more fully describe the state of the art.

The compounds of the present invention can be prepared according to the examples set out below. The examples are presented for purposes of demonstrating, but not limiting, the preparation of the compounds and compositions of this invention.

EXAMPLES

Example 1

Inhaled Sodium Pyruvate for the Treatment of Cystic Fibrosis Double Blind, Placebo-Controlled, Safety Study Sputum Inflammatory Biomarkers All of the enrolled and dosed subjects were able to provide sputum samples for analysis before and after exposure to study drug (sodium pyruvate for inhalation at 0.5, 1.5, and 5.0 mM levels). The subjects were given 5 ml samples to inhale. Specimens were of good quality for the planned assays.

The 0.5 mM levels of sodium pyruvate using 5 ml samples contain 0.28 mg of sodium pyruvate. The 5 mM levels of sodium pyruvate using 5 ml contain 2.8 mg of sodium pyruvate.

Samples were divided into two main aliquots after processing. The first aliquot was left untreated to be able to assay for the activity of free elastase. The second aliquot was treated with protease inhibitors pheylmethanesulfonylfluoride (PMSF) and ethylenediamine tetraacetic acid (EDTA) to stop any degradation of the cytokines of interest (IL-6, IL-8, IL-10, IL-17, and IL-23) and total protein.

For IL-10, IL-17 and IL-23, levels on sputum were at or below the limit of detection for the assays (7, 2 and 20 pg/mL respectively). For the other markers (total protein, elastase, IL-6, IL-8, TNF-α) levels detected where within those typically found in cystic fibrosis (CF) patients. Overall, significant changes were noted in these biomarkers tested in sputum by drug dose level or for the group as a whole (FIGS. 1-10).

FIG. 1 is a graph illustrating individual sputum total protein levels before and after study drug inhalation. Slash marks represent the median level.

FIG. 2 is a graph illustrating median change from pre- to post-study drug inhalation in sputum total protein levels and by drug dose level.

FIG. 3 is a graph illustrating individual sputum free elastase levels before and after study drug inhalation. Slash marks represent the median level.

FIG. 4 is a graph illustrating median change from pre- to post-study drug inhalation in sputum free elastase levels and by drug dose level.

FIG. 5 is a graph illustrating individual sputum IL-6 levels before and after study drug inhalation. Slash marks represent the median level.

FIG. 6 is a graph illustrating median change from pre- to post-study drug inhalation in sputum IL-6 levels and by drug dose level.

FIG. 7 is a graph illustrating individual sputum IL-8 levels before and after study drug inhalation. Slash marks represent the median level.

FIG. 8 is a graph illustrating median change from pre- to post-study drug inhalation in sputum IL-8 levels and by drug dose level.

FIG. 9 is a graph illustrating individual sputum TNF-α levels before and after study drug inhalation. Slash marks represent the median level.

FIG. 10 is a graph illustrating median change from pre- to post-study drug inhalation in sputum TNF-α levels and by drug dose level.

Given the changes noted in the cell counts (both in peripheral blood and sputum) this finding is intriguing. Since evidence for cellular influx was noted, it would have been expected to see this paralleled by a corresponding increase in cytokines and particularly in the free elastase activity. The study drug blocked this pro-inflammatory effect. The data clearly showed that pyruvate can up or down regulate inflammation depending on concentration. White blood cell counts were reduced 25% with the inhalation of 5 ml of 0.5 mM sodium pyruvate, as was total proteins, elastase, as were IL-6, IL-8, and TNF-α. White blood cell counts were increased by 25% with the inhalation of 5 ml of 5 mM pyruvate or higher as was the total proteins, elastase, IL-6, IL-8, and TNF-α.

Tissue Culture Studies

To investigate the ability of pyruvate to regulate the inflammatory process during an infection, the MatTek EpiDerm Assay was used. The MatTek Epiderm tissue samples were treated with pyruvate and the combination of pyruvate and α-ketoisovalerate both at 20 mM concentrations or higher to determine if the combination would regulate IL-1 and IL-8 up or down during a simulated infection. Following a one-hour equilibration, the Epiderm tissues were placed into the incubator (37° C., 5% $CO_2$) in assay medium. The old medium was replaced with fresh medium and the test articles were applied to the tissue samples. The test articles remained in contact with the tissue for various dosing times, one hour, then at four hours, and at 20 hours. The testing was run in duplicate. Various immunostimulators sodium dodecyl sulfate (SDS), glycoproein D (gpD) were used singly or with the α-keto acids to replicate an infection, along with vehicle controls. Untreated samples were used as negative controls. Following treatment, the media from the tissues samples were tested in Elisa kits for IL-1 and IL-8 according to the manufacture's protocols.

The 0.5 mM levels of sodium pyruvate using 5 ml samples contain 0.28 mg of sodium pyruvate. The 10 mM levels of sodium pyruvate using 5 ml contain 5.6 mg of sodium pyruvate. The 20 mM levels of sodium pyruvate using 5 ml contain 11.2 mg of sodium pyruvate. The 40 mM levels of sodium pyruvate using 5 ml contain 22.4 mg of sodium pyruvate.

A quantity of 5 ml of 0.1 mM to 100 mM of α-keto isovalerate was used. A quantity of 5 ml of 20 mM of α-keto isovalerate contains 13.8 mg. A quantity of 5 ml of 40 mM of α-keto isovalerate contains 27.6 mg. A quantity of 5 ml of 100 mM of α-keto isovalerate contains 69 mg.

Results

The primary end points were the levels of IL-8 and IL-1 after treatment with an immunostimulator, pyruvate and the combination of pyruvate and α-ketoisovalerate. The immunostimulator did not increase the cytokines by themselves. This model did not have white blood cells to respond to the immunostimulator or produce oxygen radicals. The α-keto acids did not increase the cytokines also in this model. The immunostimulators in combination with pyruvate and α-ketoisovalerate increased IL-8 over 300%, which shows direct antimicrobial activity, compared to the untreated controls. IL-8 activates neutrophils to increase their numbers at the infected site. In the same experiment, IL-1 was decreased significantly (over 200%). IL-1 increases inflammation and decreases healing times. This test clearly showed that the α-keto acids regulated the inflammatory process in dermal tissues in a manner that would increase the bodies ability to fight infected wounds and increase the body's ability to healing quicker. The same experiment was done with virally infected cells and the pyruvate and combination of pyruvate and α-ketoisovalerate decreased viral plaque formation by 50%. Viral plaques are a direct measure of viral numbers in infected cells. The antiviral drug, Acyclovir also decreased viral plaques by 60% and the α-keto acids in combination with acyclovir, totally eliminated the virus from the infected cells.

Example 2

Inhaled Sodium Pyruvate for the Treatment of Cystic Fibrosis and Other Lung Diseases Clinical Trials Cystic fibrosis (CF) is the most common, lethal inherited disease of Caucasians. Approximately 30,000 people in the United States and 70,000 worldwide have a diagnosis of CF. It is caused by mutations in the cystic fibrosis transmembrane regulator (CFTR) gene. The clinical manifestations characteristic of CF include progressive bronchiectatic lung disease with thick mucus production and colonization by *Pseudomonas aeruginosa*. The CFTR gene mutation results in altered cell transport properties, which affect both chloride and glutathione secretion. Chronic inflammation, associated with activated neutrophils and macrophages, is a common feature of CF. Highly reactive toxic oxygen (superoxide anion, free hydroxyl required hydrogen peroxide) and nitrogen species (NO peroxynitrites) are abundant in the chronic inflammatory response in CF and appear to playa prominent role in the pathogenesis of this disease as are excess levels of inflammatory cytokines.

A total of 15 CF patients were treated with varying doses of sodium pyruvate. The therapeutic dose, 0.5 mm lowered the inflammatory cytokines (markers) including, IL-6, IL-8 and the 5 mm sodium pyruvate increased all the inflammatory markers. The 0.5 mm can be used in CF patients to lower inflammation and white blood cell numbers and the 5 mm can be used to increase cytokines and white blood cell numbers needed to fight infections.

Treatment of HSV-I Infected Cell with Various α-Keto Acids

α-Keto Acids Regulation of Inflammatory Anti Viral Cytokines at Varying Mm Concentrations α-Keto Acids Tested Alone for their Ability to Reduce Viral Plaques (Numbers Live Viruses)

Percentage of Viral Plaque Reduction in Virally Infected Cells

|  | pyruvate | α-keto isovalerate | α-keto butyrate | pyruvate + α-keto isovalerate | pyruvate + α-keto butyrate |
| --- | --- | --- | --- | --- | --- |
| 05 mM | 5% | 0% | 0% | 10% | 0% |
| 10 mM | 10% | 5% | 0% | 20% | 3% |
| 20 mM | 38% | 10% | 0% | 50% | 30% |
| 40 mM | 50% | 20% | 5% | 74% | 40% |

α-Keto Acids in Combination with Acyclovir
(Therapeutic Dose)

Percentage of Viral Plaque Reduction in Virally
Infected Cells (Reduction of Live Viruses)

|  | Pyruvate Acyclovir | α-keto isovalerate Acyclovir | α-keto butyrate Acyclovir | therapeutic dose Acyclovir alone |
|---|---|---|---|---|
| 10 mM | 66% | 42% | 39% | 40% |
| 20 mM | 90% | 55% | 40% |  |

α-Keto Acids Combinations with Acyclovir

Percentage of Viral Plaque Reduction in Virally
Infected Cells

|  | Pyruvate α-keto isovalerate Acyclovir | Pyruvate α-keto butyrate Acyclovir |
|---|---|---|
| 10 mM | 78% | 63% |
| 20 mM | 100% | 70% |

The results clearly show that pyruvate was the only α-keto acid that increased the inflammatory cytokines high enough needed to kill high numbers of the virus in virally infected cells as measured by reduction in viral plaques. Acyclovir a known anti-viral agent, did reduce viral plaques also. Unexpectedly, the combination of pyruvate and α-keto isovalerate produced the best results, by totally eliminating the virus from the infected cells. Inhalation of pyruvate at 0.5 mM reduced the levels of white blood cells, elastase, IL-8, IL-6 and did not increase levels of TNF-α. Inhalation of 5 mM of pyruvate in humans increased levels of white blood cells elastase, IL-8, IL-6 and TNF-α (cytokines), that would be used to kill viruses in the lungs. This tissue culture data along with data from humans, confirms that some α-keto acids worked and some like α-keto butyrate did not. It appears that α-keto butyrate will reduce inflammation and the production of cytokines, even during an infection.

REFERENCES

1. Hardman, J. et al., The pharmacological basis of therapeutics. Ninth edition 1996, pp. 137-356.
2. Moncada, S. et al, Nitric Oxide: physiology, pathophysiology, and pharmacology. 1991 Pharmacological Reviews Vol. 43 no pp 109-141.
3. Nathan, C., Nitric oxide as a secretory product of mammalian cells. FASEB Journal vol. Sep. 6, 1992 pp 3051-3064.
4. Rossaint, R. et al, Inhaled nitric oxide: its effect on pulmonary circulation and airway smooth muscle cells. Euro Heart Jour. 1993 vol. 14 Supp. pp 133-140.
5. Mattes, K. et al, NO in exhaled air is correlated with markers of eosinophilic airway inflammation in corticosteroid-dependent childhood asthma. Euro Respir J. 1999 vol. 13, pp 1391-1395
6. Artlich, A. et al., Childhood asthma: exhaled nitric oxide in relation to clinical symptoms. Euro Respir. J. Vol. 13, pp 1395-1401.
7. Jobsis, Q. et al. Sampling of exhaled nitric oxide in children: end expiratory plateau, balloon and tidal breathing methods compared. Euro Respir. J. Vol. 13, pp 1406-1410.
8. Mukala, K. et al. Personally measured weekly exposure to $NO_2$ and respiratory health among preschool children. Euro. Respir. J. Vol. 13, pp 1411-1417.
9. Stanko R., The power of Pyruvate 1999, Keats Publishing.
10. Kelly, F. et al. Antioxidant kinetics in lung ravage fluid following exposure of humans to nitrogen dioxide. Am. J. Respir. Crit. Med. Vol. 154 1991 pp 1700-1705.
11. Roberts, J. et al. Inhaled nitric oxide and persistent pulmonary hypertension of the new borns. The new England Journal of Medicine Feb. 27, 1997 pp 605-610.
12. Lehninger 1981 Biochemistry, Worths Publishing.
13. Comhair, S. et al. Rapid loss of superoxide dismutase activity during antigen-induced asthmatic response. Lancet vol. 355 Feb. 192000.
14. Stewart R M, et al., Hydrogen peroxide contracts airway smooth muscle: a possible endogenous mechanism. Respir. Physiol 1981 45: 333-342.
15. Rhoden K J, Barnes P J: Effect of hydrogen peroxide on guinea pig tracheal smooth muscle in vitro: role of cyclooxygenase and airway epithelium. Br. J. Pharmacol 1989 98: 325-330
16. Motojima S, et al. Toxicity of eosinophil cationic proteins for guinea pig tracheal epithelium in vitro. Am Rev Respir Dis 1989 139: 801-805
17. Sporn P H, et al. Hydrogen peroxide induced arachidonic acid metabolism in rat alveolar macrophage. Am Rev Respir Dis 1988 137: 49-56
18. Postma, D. S. et al Association between nonspecific bronchial hyperreactivity and superoxide anion production by polymorphonuclear leukocytes in chronic air flow obstruction. Am. Rev Respirdis. (1988) 137: 57-61.
19. Alving, K. Methodological aspects of exhaled nitric oxide measurements Euro Respir Rev 1999: 9:68, 208-211
20. Kharitonov, S. Exhaled nitric oxide and carbon monoxide in asthma. Euro Respir. Rev. 1999, 9:68, 212-216.
21. Gouw, P. et al. Stimuli affecting exhaled nitric oxide in asthma. Euro Respir. Rev. 1999; 9:68, 219-222.
22. Kharitonov, S. Exhaled nitric oxide and carbon monoxide in respiratory diseases. Euro Respir. Rev. 1999; 9:68, 223-226.
23. Barnes, P. The effect of drugs on exhaled nitric oxide. Euro Respir. Rev. 1999; 9:68, 231-233.
24. Baraldi, E. et al. Application of exhaled nitric oxide measurement in pediatrics. Euro Respir. Rev. 1999; 9:68, 234-240.
25. Lundberg, J. Nitric oxide in the nasal airways. Euro Respir. Rev. 1999; 9:68, 241-245
26. Culpitt, S. The measurement of hydrogen peroxide in airways disease. Euro Respir. Rev. 1999; 9:68, 246-248.
27. Montuschi, P. Isoprostanes and other exhaled markers in respiratory diseases. Euro Respir. Rev. 1999; 9:68, 249-253.
28. Robertson, F M, Gene expression and cellular sources of inducible nitric oxide synthase during tumor promotion. Carcinogenesis September; 1996 17 (9): 2053-9.
29. Soler, M N, et al, Gene therapy of rat medullary thyroid cancer by naked nitric oxide synthase II DNA injection. J Gene Med September-October; 2000 2(5): 433-52. and sinusoidal cytotoxicity: a natural hepatic defense against metastasis. Cancer Res Oct. 15, 200060(20): 5862-9.
30. Wang H H, B 16 melanoma cell arrests in mouse liver induces nitric oxide release and sinusoidal cytotoxicity: a natural hepatic defense against metastasis. Cancer Res Oct. 15, 200060(20): 5862-9.

31. Brennan P A., The action and interactions of nitric oxide in solid tumors. Eur J Surg Oncol Aug. 26, 2000 (5): 434-7.
32. Rieder J, et al. Different patterns of inducible nitric oxide synthase gene expression in ovarian carcinoma cell lines. Anticancer Res September-October; 2000 20(5A): 3251-8.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

I claim:

1. A method for treating a pulmonary and upper respiratory disease state in mammals, said disease state characterized by abnormally low levels of inflammatory agents, said method comprising:
   contacting the mammalian cells with an inflammatory regulator comprising at least 2.8 mg pyruvate, a pyruvate precursor, or a salt thereof;
   wherein the inflammatory agents which are at abnormally low levels are selected from the group consisting of elastase, white blood cells, and cytokines selected from the group consisting of interleukin-6, interleukin-8, interleukin-10, interleukin-17, interleukin-23 and tumor necrosis factor-$\alpha$;
   wherein the disease state is chronic obstructive pulmonary disease (COPD).

2. The method according to claim 1, wherein the cytokine is selected from the group consisting of interleukin-6, interleukin-8, interleukin-10, interleukin-17, and interleukin-23.

3. The method according to claim 2, wherein the cytokine is selected from the group consisting of interleukin-6, and interleukin-8.

4. The method according to claim 1, wherein the cytokine is tumor necrosis factor-$\alpha$.

5. The method according to claim 1, wherein the inflammatory agent is selected from the group consisting of elastase, and white blood cells.

6. The method according to claim 1, wherein the pyruvate is selected from the group consisting of pyruvic acid, lithium pyruvate, sodium pyruvate, potassium pyruvate, magnesium pyruvate, calcium pyruvate, zinc pyruvate, manganese pyruvate, aluminum pyruvate, ammonium pyruvate, and mixtures thereof.

7. The method according to claim 1, wherein the pyruvate precursors are selected from the group consisting of pyruvyl-glycine, pyruvyl-alanine, pyruvyl-leucine, pyruvyl-valine, pyruvyl-isoleucine, pyruvyl-phenylalanine, pyruvamide, salts of pyruvic acid, and mixtures thereof.

8. The method according to claim 1, wherein the inflammatory regulator contains from about 2.8 mg to about 1 gram of pyruvate, a pyruvate precursor, or a salt thereof.

9. The method according to claim 1 further comprising contacting the mammalian cells with a therapeutic agent.

10. The method according to claim 9, wherein the therapeutic agent is a steroid.

11. The method according to claim 9, wherein the therapeutic agent is administered prior to administration of the inflammatory regulator.

12. The method according to claim 9, wherein the therapeutic agent is administered concomitantly with administration of the inflammatory regulator.

13. The method according to claim 9, wherein the therapeutic agent is administered after administration of the inflammatory regulator.

* * * * *